(12) United States Patent
Eidel et al.

(10) Patent No.: US 9,746,449 B2
(45) Date of Patent: Aug. 29, 2017

(54) ULTRASONIC SENSOR DEVICE HAVING AN IMPROVED DECOUPLING RING AND MOTOR VEHICLE

(71) Applicant: Valeo Schalter Und Sensoren GmbH, Bietigheim-Bissingen (DE)

(72) Inventors: Oliver Eidel, Moglingen (DE); Stefan Triebl, Muhlacker (DE); Hans Wilhelm Wehling, Heilbronn (DE); Thomas Jung, Heilbronn (DE); Hubert Neft, Grossbottwar (DE); Stephan Max, Gifhorn (DE)

(73) Assignee: Valeo Schatter Und Sensoren GmbH, Bietigheim-Bissingen (DE)

( * ) Notice: Subject to any disclaimer, the term of this patent is extended or adjusted under 35 U.S.C. 154(b) by 292 days.

(21) Appl. No.: 14/415,872

(22) PCT Filed: Jul. 23, 2013

(86) PCT No.: PCT/EP2013/065501
§ 371 (c)(1),
(2) Date: Apr. 2, 2015

(87) PCT Pub. No.: WO2014/016288
PCT Pub. Date: Jan. 30, 2014

(65) Prior Publication Data
US 2015/0185188 A1  Jul. 2, 2015

(30) Foreign Application Priority Data

Jul. 24, 2012 (DE) ........................ 10 2012 106 696

(51) Int. Cl.
*G01S 7/521* (2006.01)
*G01S 15/93* (2006.01)
*G01N 29/32* (2006.01)

(52) U.S. Cl.
CPC .............. *G01N 29/32* (2013.01); *G01S 7/521* (2013.01); *G01S 15/931* (2013.01); *G01N 2291/023* (2013.01)

(58) Field of Classification Search
CPC ....... G01S 15/931; G01S 7/521; G01N 29/32; G01N 2291/023
(Continued)

(56) References Cited

U.S. PATENT DOCUMENTS 7,832,273 B2 * 11/2010 Schaaf .................. B60R 19/483
                                                              73/584
8,059,490 B2 * 11/2011 Rapps .................... H04R 17/00
                                                              367/140

(Continued)

FOREIGN PATENT DOCUMENTS

DE           42 38 924 A1     5/1994
DE    10 2009 046 972 A1     5/2011
(Continued)

OTHER PUBLICATIONS

International Preliminary Report on Patentability (Chapter I of the Patent Cooperation Treaty) for International Application No. PCT/EP2013/065501, filed Jul. 23, 2013, Valeo Schalter Und Sensoren GmbH.

*Primary Examiner* — J M Saint Surin
(74) *Attorney, Agent, or Firm* — Womble Carlyle Sandridge & Rice, LLP (57) ABSTRACT

The invention relates to an ultrasonic sensor device (1) for a motor vehicle, comprising an ultrasonic sensor (2), which comprises a pot-shaped membrane (21) for emitting and/or receiving ultrasonic signals, comprising a decoupling ring (6), which is arranged to fit around the membrane (21) in contact with an outer circumference (34) of the membrane (21), and comprising a stiffening element (13), which is arranged around the decoupling ring (6), wherein the decou- (Continued)

pling ring (6) comprises a circumferential first radial decoupling region (32) which is in contact with the outer circumference (34) of the membrane (21) as well as a second radial decoupling region (33) with an axial face (37) which is in contact with an axial face (38) of the stiffening element (13).

17 Claims, 7 Drawing Sheets

(58) Field of Classification Search
USPC .......................................................... 73/617
See application file for complete search history.

(56) References Cited

U.S. PATENT DOCUMENTS

| | | | | |
|---|---|---|---|---|
| 8,973,442 B2* | 3/2015 | Schneider | ............... | G01S 7/521 367/140 |
| 2009/0314575 A1* | 12/2009 | Reiche | ................... | G10K 9/122 181/148 |
| 2010/0296692 A1* | 11/2010 | Reiche | ................... | H04R 31/00 381/423 |
| 2012/0304772 A1 | 12/2012 | Schneider et al. | | |
| 2015/0192673 A1* | 7/2015 | Wehling | ................ | B60R 19/483 367/138 |
| 2015/0198698 A1* | 7/2015 | Wehling | ................... | G01S 7/521 73/632 |

FOREIGN PATENT DOCUMENTS

| | | |
|---|---|---|
| DE | 10 2010 044 996 A1 | 3/2012 |
| DE | 10 2010 045971 A1 | 3/2012 |
| DE | 102010045971 A1 * | 3/2012 |
| DE | 10 2011 105 013 A1 | 12/2012 |
| GB | 2 272 819 A | 5/1994 |
| WO | WO0212027 * | 2/2002 |
| WO | WO 2009/144545 A1 | 12/2009 |
| WO | WO 2013/117442 A1 | 8/2013 |

* cited by examiner

ULTRASONIC SENSOR DEVICE HAVING AN IMPROVED DECOUPLING RING AND MOTOR VEHICLE

The invention relates to an ultrasonic sensor device for a motor vehicle, comprising an ultrasonic sensor, which comprises a pot-shaped membrane for emitting and/or receiving ultrasonic signals, comprising a decoupling ring, which is arranged to fit around the membrane in contact with an outer circumference of the membrane, and comprising a stiffening element, which is arranged around the decoupling ring and is preferably formed from ceramic. The invention moreover relates to a motor vehicle comprising such ultrasonic sensor device.

Ultrasonic sensors are mounted in the known way in the front portion and in the rear portion of the vehicle, in particular on bumpers. They are assigned to driver assistance devices and provide information about the environment of the vehicle, namely about the distances between the motor vehicle, on the one hand, and the obstacles present in its environment, on the other hand. Driver assistance devices can be for instance parking assistance systems, systems for monitoring dead angles, headway control systems, lane monitoring systems, braking assistance systems, and the like.

It is already prior art that such ultrasonic transducers are mounted into the bumpers to be unconcealed and thus visible. This means that they are arranged in open recesses in the bumper and are visible from the outside. A pot-shaped membrane of the ultrasonic sensor extends here through the open recess of the bumper so that the front side of the membrane, via which ultrasonic waves are emitted and received, are flush with the outer surface of the bumper. These ultrasonic sensors, however, have the decisive disadvantage that they are arranged to be visible and thus impair the overall optical impression of the motor vehicle.

For this reason the interest in the present case is focused on ultrasonic transducers that are mounted to be concealed or hidden and which are not visible when the bumper is viewed from the outside and are covered by the bumper. Here the ultrasonic sensor is present on a back side of the bumper so that the front side of the membrane—possibly via an additional mounting lid—is brought into contact with the back side of the bumper.

In the case of ultrasonic sensors mounted in such a way directly behind the bumper the ultrasonic signals are emitted and received through the material of the bumper. Thus, a portion of the bumper vibrates together with the membrane. It is thus frequently required that this vibrating portion of the bumper is delimited with the aid of a stiffening element formed from ceramic. It is for instance known to provide a stiffening element formed from ceramic, which has a through-opening, through which the pot-shaped membrane of the ultrasonic sensor extends so that the stiffening element is arranged around the membrane and moreover—if given, via a mounting lid—is brought into contact with the back side of the bumper. Thus, in the case of sensors that are mounted to be concealed behind the bumper, though, considerably higher requirements are given with regard to positioning, adhesion, and the tolerances now to be kept. The ultrasonic sensor must be attached mechanically fixed behind the bumper. This is required to allow for loss-free emission by the ultrasonic sensor through the bumper. In order to keep the emission and receiving losses down, the emission surface of the ultrasonic sensor—i.e. the front surface of the membrane—must be firmly connected with the bumper or else be designed with a loss-free coupling element or mounting lid between the front side of the membrane and the bumper. In order to keep the introduced vibrations local and to influence the emission characteristic, for this purpose the above-named stiffening element with a large e-module closely fit around the transducer or the membrane is required. Also this stiffening ring must be mechanically firmly connected to the bumper or the holder.

A covered arrangement of an electroacoustic transducer is known for instance from the DE 42 38 924 A1.

In the present case the focus is in particular on ultrasonic sensors which are arranged to be concealed on the back side of the trim element and emit or receive ultrasonic signals through the material of the trim element. On the one hand, in the case of such ultrasonic sensors a decoupling ring fit around the membrane is required for the vibration of the membrane not to be transferred to other, adjacent components, but to be kept only local; on the other hand, in particular in the case of concealed sensors a stiffening element—for instance made from ceramic as in document DE 42 38 924 A1—fit around the ultrasonic sensor is required so that the resonating portion of the trim element can be limited to a defined portion. Now it has turned out that in the case of ultrasonic sensors with a concealed arrangement, in which the ultrasonic waves are emitted through the material of the trim element, a certain portion of the ultrasonic waves are not emitted towards the front, i.e. through the trim element, but towards the back—quasi in the direction of the interior of the vehicle—as undesired echo. Whilst the primary radiation and the major portion of the radiation of the ultrasonic signals occurs through the trim element, also a considerable portion of the sound energy is given off into the space behind the trim element. This energy then reflects from body elements of the vehicle and returns to the ultrasonic sensor as reflections, which can lead to pseudo echoes or fake targets in the close range and thus to a function failure of the respective driver assistance system, namely for instance the automatic parking assistance system. A particular challenge thus consists in avoiding a propagation of the ultrasound given off by the ultrasonic sensor towards the back and to preferably reduce it to an amount (in dB) below the receiving threshold of the sensor.

It is the task of the invention to provide a solution as how to be capable of reducing the portion of the sound energy given off towards the back or the echo in comparison with the prior art in the case of an ultrasonic sensor device of the initially mentioned kind.

According to the invention this task is solved by an ultrasonic sensor device with the features according to patent claim 1. Advantageous embodiments of the invention are subject matter of the dependent patent claims, the description, and the figures.

According to the invention an ultrasonic sensor device for a motor vehicle comprises an ultrasonic sensor, which comprises a pot-shaped membrane for emitting and/or receiving ultrasonic signals, as well as a decoupling ring, which is arranged to fit around the membrane in contact with an outer circumference of the membrane, as well as a stiffening element, which is arranged around the decoupling ring. The decoupling ring has a circumferential first radial decoupling region, which is in contact—in particular fully circumferentially—with the outer circumference of the membrane as well as a second radial decoupling region with an axial face, which is in contact with an axial face of the stiffening element.

In an advantageous way by such a design of the decoupling ring an axial touch or an axial contact between the decoupling ring, on the one hand, and the stiffening element, on the other hand, is achieved, whereby the region of the membrane can be particularly effectively acoustically sealed toward the back. Thus, the ultrasound given off towards the back is reliably subdued so that a sound propagation in the direction of the interior of the vehicle can be prevented or at least clearly reduced. This is because the second decoupling region can be axially pressed in between a housing of the ultrasonic sensor, on the one hand, and the axial face of the stiffening element, on the other hand.

Preferably, it is envisaged in this connection that the axial face of the decoupling ring forms a front side, which faces in the direction of a trim element of the motor vehicle and thus is in contact with a back side of the stiffening element that faces the ultrasonic sensor and faces away from the trim element.

This means that the decoupling ring quasi has two different functions: On the one hand, the decoupling ring prevents the membrane from touching the adjacent components, and also provides for the vibration of the membrane not to be transferred to the adjacent components. On the other hand, the decoupling ring also prevents a radiation of the ultrasound towards the back in the direction of the interior space of the vehicle.

Such acoustic sealing may also be used for preventing humidity from entering the region of the membrane. Thus also ice bridges can be prevented, which could impair the functioning of the ultrasonic sensor device.

Consequently, the decoupling ring has two radial decoupling regions, namely a first decoupling region that is in contact with the outer circumference of the membrane, as well as a second radial decoupling region that is arranged around this first decoupling region and the axial face of which is in contact with the axial face of the stiffening element. In one embodiment it may be envisaged that the second decoupling region is formed by at least one side bar or collar that is arranged radially spaced apart from the first decoupling region and extends in the axial direction and the axial face or tip side of which is in contact with an axial face of the stiffening element. By such side bar thus a sealing rib is formed, through which the region of the membrane is acoustically sealed off towards the back. Thus, moreover it can be achieved that—from a cross-sectional point of view—the decoupling ring has merely a dot-shaped or spotty place contacting the stiffening element, namely on the axial face front side. Such axial contact with the stiffening element allows for an enhanced sealing against echo.

In this context it has turned out to number five be advantageous, if the at least one side bar is designed to taper off towards axial face. Precisely in this case the tip-like or tip-shaped axial face of the side bar can be created, which is in contact with the axial face of the stiffening element. Thus, a sound attenuation structure is created, with which the echo is clearly reduced in comparison with the prior art.

With regard to the design of the second radial decoupling region now two different embodiments may be envisaged.

On the one hand, it may be envisaged that the second radial decoupling region is formed by a single side bar that is designed circumferentially around the first decoupling region and the axial face of which in the form of a ring is circumferentially in contact with the axial face of the stiffening element. Thus, a contact spot between the side bar and the stiffening element is designed that is ring-shaped and 360° circumferential. Such design provides reliable acoustic sealing, on the one hand; and, on the other hand, thus also a sealing against humidity can be facilitated so that ice bridges can be avoided.

On the other hand, for a reliable acoustic sound attenuation it may also be envisaged that at least two such side bars are arranged spaced apart from each other in the circumferential direction, each of which comprise an axial face, which is brought into contact with the axial face of the stiffening element. Thus, several contact spots are designed, which are distributed in the circumferential direction between the second radial decoupling region, on the one hand, and the stiffening element, on the other hand. Also this material-saving design of the decoupling ring provides an effective sound sealing of the region of the membrane.

It is preferred if the first radial decoupling region is arranged at a radial distance from the stiffening element so that in particular the decoupling ring touches the stiffening element exclusively via the second decoupling region. Thus, a circumferential radial air gap is formed between the stiffening element, on the one hand, and the first radial decoupling region. It namely has turned out that such design secures reliable oppression of the echo.

It has turned out to be particularly advantageous if the second decoupling region comprises a radially outward protruding or outwardly extending sealing lip, which is in contact with a radial inner circumference of the stiffening element and thus interacts in a sealing way with it. This means that this sealing lip preferably belongs to the above-named side bar. In this embodiment the decoupling ring consequently is pressed in or jammed in particular both axially between the sensor housing and the axial face of the stiffening element as well as radially between the membrane and the stiffening element. By providing such an—in particular circumferential—sealing lip the propagation of sound waves in the direction of the vehicle's interior space can be nearly completely oppressed. The sealing lip in this connection can extend at an angle radially outward so that both an axial as well as a radial direction component of the extension is given. Then the sealing lip is more easily inserted into the through-opening of the stiffening element.

Preferably, the decoupling ring is formed from a soft elastic material, in particular from silicone and/or from TPE plastic (thermoplastic elastomers). A soft elastic material besides a particularly good sound oppression here also allows for a reliable sealing against liquids. The properties of such a material moreover remain consistent across a relatively large temperature range. By such soft elastic material moreover the adhesion of the membrane is not impaired. Not least, such a material can be pressed in and thus has a resilient effect, which additionally supports the acoustic and/or liquid sealing.

In one embodiment of the invention it is envisaged that the ultrasonic sensor device comprises a holder for the ultrasonic sensor. The holder can comprise a receiving part with a receptacle for the stiffening element. Between a bottom of the receptacle and a back side of the stiffening element that faces the ultrasonic sensor an attenuation disk can be arranged, which is designed for attenuating the echo. Thus, optionally also the remaining vibrations given off in the backward direction can be attenuated. Such attenuation disk consequently allows for the reduction of the echo to a minimum.

Preferably, the attenuation disk is formed from a soft elastic material, namely for instance from silicone and/or from TPE plastic. This means it may be formed from the same material as the decoupling ring. By such a soft elastic material it can here be accomplished that the attenuation disk is jammed between the bottom of the receiving element, on the one hand, and the back side of the stiffening ring, on the other hand, so that besides a reliable sound attenuation also a tolerance compensation in the mounted state can be achieved.

It has proven particularly advantageous if the attenuation disk on its—in particular entire or complete—front side, which faces the stiffening element, has a sound reduction structure, via which the attenuation disk contacts the back side of the stiffening element only in a dot-shaped or spotty manner. Such a sound reduction structure can for instance be formed by a knob structure and thus by a plurality of knobs, which are—in particular regularly—arranged on the front side of the attenuation disk distributed in a common plane. These knobs consequently face in the direction of the stiffening element and contact the back side of the stiffening element with their tips. Such a surface, which comprises a surface structure that is specific to the stiffening element— such as for instance knob geometry—, prevents a touching of surfaces of the front side of the attenuation disk and the back side of the stiffening element and thus also deflects the echo in various directions so that the energy of this sound signal is reduced. A single knob in this connection can have a cross-section to the effect that the walls or legs forming the knob form an angle of for instance 50° to 70°, in particular an angle of 60°.

With regard to the design of the attenuation disk now various embodiments are envisaged:

The attenuation disk can be designed as a component that is separate from the receiving element. Such an attenuation disk without much effort can be inserted between the bottom of the receiving element, on the one hand, and the stiffening element, on the other hand, so that it is brought into contact with the surface of its preferably even and smooth back side with the bottom of the receiving element. Here the attenuation disk can for instance be glued to the bottom.

Alternatively it may also be envisaged that the attenuation disk is injection moulded on the bottom of the receptacle of the receiving element. In this integrally formed design it can be done without an additional component so that the mounting of the ultrasonic sensor device is rendered easier and the mounting time reduced.

The attenuation disk can also be integrally formed with the decoupling ring. Thus, the number of required components is minimal.

Alternatively, it may be envisaged that the attenuation disk is designed as a component that is separate from the decoupling ring. This embodiment proves advantageous for instance in the case of a somewhat thicker stiffening element, in which possibly a somewhat larger distance between the decoupling ring and the attenuation disk is envisaged.

A motor vehicle according to the invention comprises an inventive ultrasonic sensor device.

The preferred embodiments presented with regard to the ultrasonic sensor device according to the invention and their advantages in analogy apply to the inventive vehicle.

In the vehicle it may be provided that the ultrasonic sensor device is arranged to be concealed on a back side of a trim element, for instance a bumper, of the vehicle so that the ultrasonic signals of the ultrasonic sensor are emitted and/or received through the material of this trim element. The front side of the membrane in this connection can be brought into direct contact with the back side of the trim element or be coupled via a mounting lid of the above-named holder with the back side of the trim element.

Further features of the invention derive from the claims, the figures, and the description of the figures. All features and feature combinations previously named in the description as well as named in the following in the description of the figures and/or shown in the figures alone are employable not only in the respective indicated combination but also in other combinations or taken alone.

The invention is now explained in more detail by reference to a preferred embodiment as well as by reference to the enclosed drawings.

It is shown in.

In the figures same elements or elements having the same function are equipped with the same reference signs.

Figure 1:
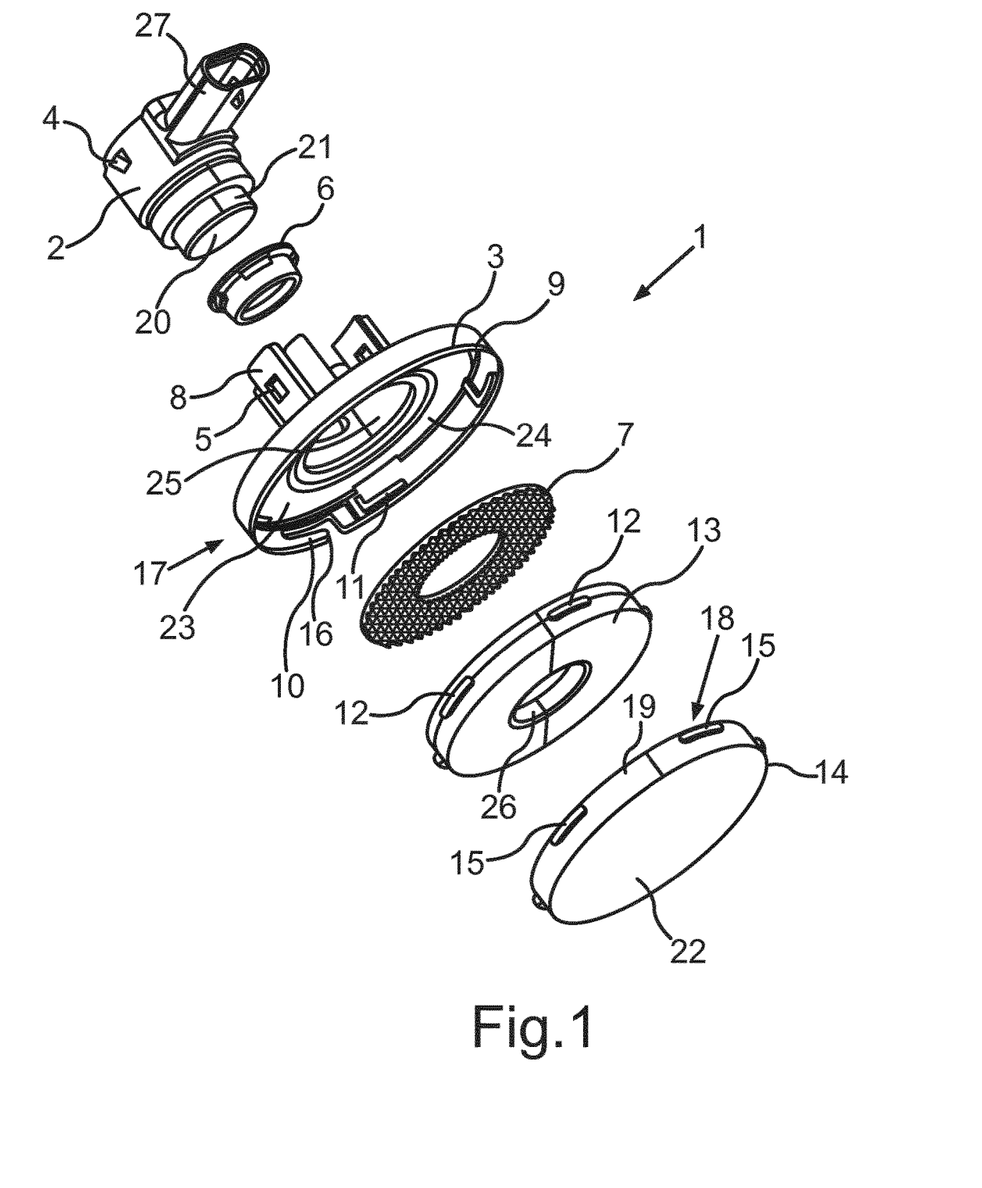
FIG. 1 a schematic exploded view of an ultrasonic sensor device according to an embodiment of the invention.

FIG. 1 shows an ultrasonic sensor device 1 in a schematic exploded view. This comprises an ultrasonic sensor 2, which is capable of being fastened releasably in a non-destructive way in a receiving element 3, namely capable of being latched-in. For this purpose for instance two latch-on elements 4 are designed on the ultrasonic sensor 2, which are provided for latching into the corresponding latch-in lugs 5 of a receiving duct 8 of the integrally formed receiving element 3 made from plastic.

The ultrasonic sensor device 1 also comprises a decoupling ring 6 as well as optionally an attenuation disk 7.

The receiving element 3 moreover comprises a base 9, which is of a cylindrical design and has a larger diameter than the receiving duct 8. On an edge 10 the base 9 latch-in structures 11 are designed on an inner circumference, into which latch-in elements 12 of a stiffening element 13, which is ring-shaped and disk-shaped and formed from ceramic, can be latched. Optionally, also a mounting lid 14 can be provided, which can be integrally formed from plastic and via its latch-in elements 15 can possibly be latched into the latch-in structures 11 or else into other latch-in openings 16 of the base 9. If such a mounting lid 14 is used, it can possibly be done without the latch-in elements 12 of the stiffening element 13.

A holder 17 is formed by the receiving element 3 as well as optionally by the mounting lid 14. Thereby a highly flexible and variable embodiment of the ultrasonic sensor device 1 can be ensured and the most varied mounting options of the ultrasonic sensor device 1 be facilitated in the most different mounting positions or mounting situations on a trim element of a motor vehicle.

The stiffening element 13 is designed as a separate component and for instance made from ceramic. It serves, on the one hand, for attenuating the vibration transfer to the trim element; on the other hand, it serves for the limitation of the signal radiation of the ultrasonic sensor 2.

The mounting lid 14 on its back side, which faces the ultrasonic sensor 2, has an indentation, which on the side of the circumference is fully circumferentially limited by a side bar 19, upon which the latch-in elements 15 are moulded. In the mounted state the ultrasonic sensor 2 extends into this indentation so that a front side 20 of a pot-shaped membrane 21 of the ultrasonic sensor 2 is in contact with the back side 18 of the mounting lid 14. A front side 22 of the mounting lid 14 then is in contact with the back side of the trim element. If no such mounting lid 14 is used, the front side 20 of the membrane 21 is directly glued together with the back side of the trim element.

The membrane 21 for instance is entirely manufactured from aluminium.

As can be further seen from FIG. 1, the base 9 of the receiving element 3 on its side facing the stiffening element 13 has a receptacle 23, which has a bottom 24. In the bottom 24 an opening 25 is formed, through which the membrane 21 extends in the mounted state, in order to come into contact with the back side 18 of the mounting lid 14 or else with the back side of the trim element. A corresponding through-opening 26 is also designed in the ceramic stiffening element 13.

The ultrasonic sensor 2 moreover has a plug 27, via which the ultrasonic sensor 2 can be electrically coupled with the electronic control device of the motor vehicle.

Now the focus is on the decoupling ring 6 as well as the attenuation disk 7. Both components can be formed from a soft elastic material, such as for instance silicone and/or from a TPE plastic, i.e. a thermoplastic elastomer.

Figure 6:
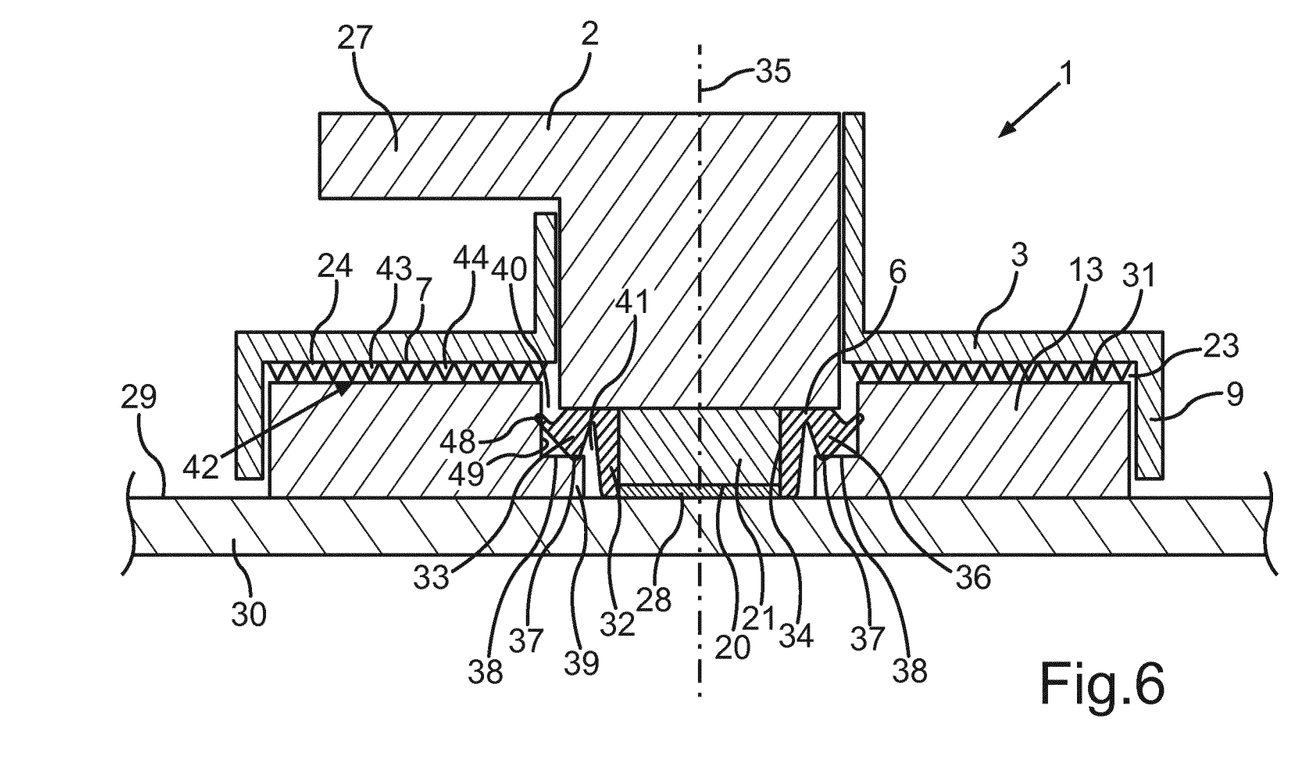
FIG. 6 a schematic sectional view of an ultrasonic sensor device.

With reference to FIG. 6, in which a sectional view of the ultrasonic sensor device 1 is shown, the design of the decoupling ring 6 is now explained in more detail. In the design according to FIG. 6 the mounting lid 14 has been left out so that the pot-shaped membrane 21 is connected via an adhesive layer 28 with a back side 29 of a trim element 30 designed as a bumper. Thus, the front side 20 of the membrane 21 is in contact with the back side 29. Around the membrane 21 the decoupling ring 6 is arranged and around this decoupling ring 6 again the stiffening element 13 made from ceramic is arranged. This stiffening element 13 is placed in the receptacle 23 of the base 9 of the receiving element 3. The attenuation disk 7 therein is arranged between a back side 31 of the stiffening element 13, on the one hand, and the bottom 24 of the receptacle 23, on the other hand.

Figure 7:
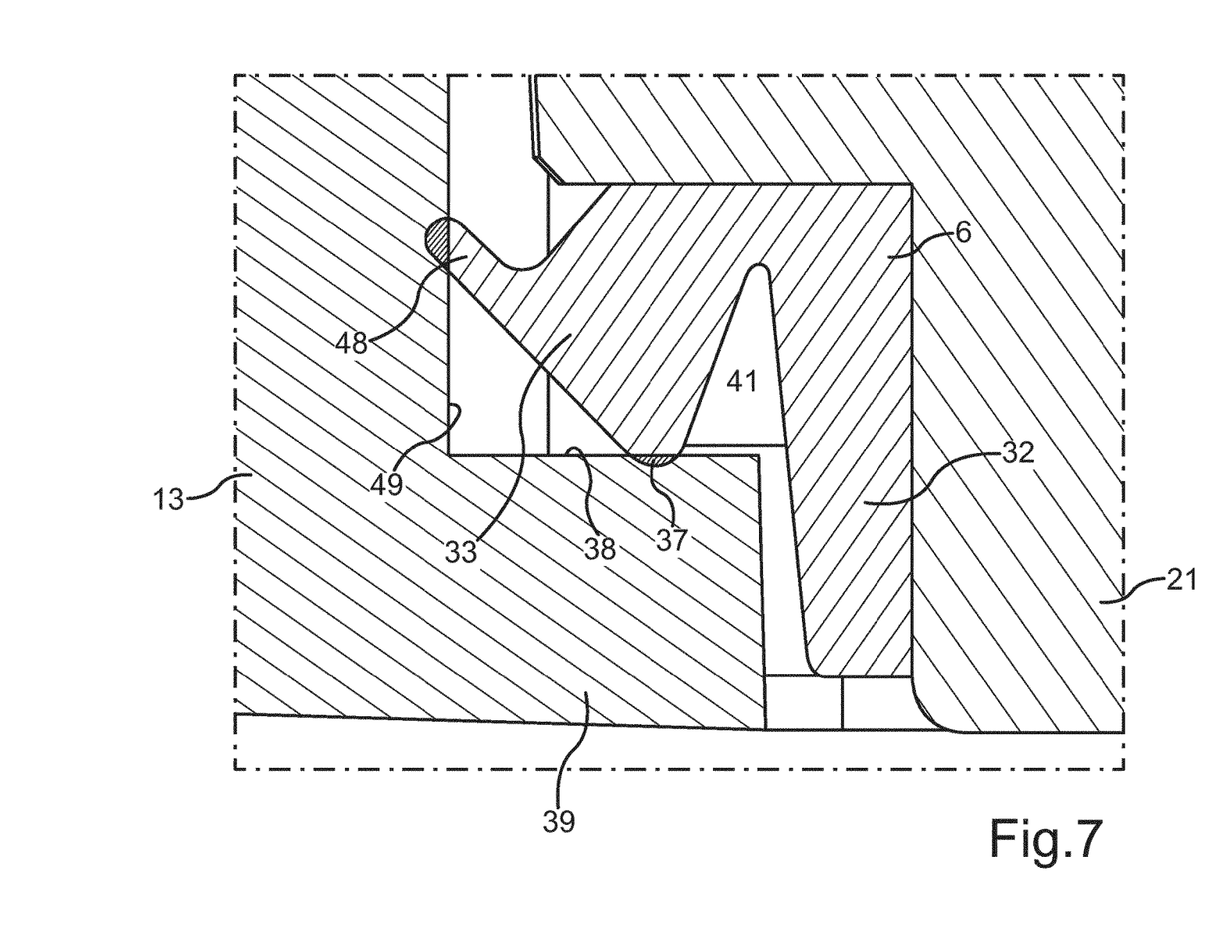
FIG. 7 an enlarged view of a portion of the ultrasonic sensor device according to FIG. 6.

As can be seen from FIG. 6 as well as from the enlarged view according to FIG. 7, the decoupling ring 6 in the embodiment consists of two radial regions, namely a first radial decoupling region 32 as well as a second radial decoupling region 33. The first decoupling region 32 is in contact with an outer circumference of the pot-shaped membrane 21. This first decoupling region 32 therein is designed to be fully circumferential so that it encompasses or encloses the membrane 21 entirely.

By contrast, the second decoupling region 33 is arranged at a radial distance from the membrane 21 and moreover at a radial distance from the first decoupling region 32. The second decoupling region 33 is essentially designed in the form of (at least) one side bar 36 extending in the axial direction or along a longitudinal axis 35 of the ultrasonic sensor 2 and facing in the direction of the trim element 30 and has a tip-shaped axial face 37 at the front, which faces the trim element 30 and is brought into dot-shaped contact with the axial face 38 of a radial protrusion 39 of the stiffening element 13. This axial face 38 of the protrusion 39 at the same time forms a back side of the protrusion 39 or of the stiffening element 13, which faces the ultrasonic sensor 2. The protrusion 39 therein is formed in that on the inner circumference 49 of the stiffening element 13 a cornered or rectangle recess 40 is designed. This recess 40 is designed to be circumferential so that also the recess 39 extends circumferentially around the membrane 21.

Accordingly, the at least one side bar 36 has a tip on the axial face 37, which is in contact with the axial face 38 of the protrusion 39. In this connection the side bar 36 is designed to be tapered in the direction of the protrusion 39 of the stiffening element 13 and thus in the axial direction towards the axial face 37 so that the side bar 36 has various radial widths along the longitudinal axis 35. This side bar 36 extends also in parallel to the first decoupling region 32, which is in contact with the outer circumference 34 of the membrane 21. On the whole, thus between the first and the second decoupling region 32, 33 a circumferential, O-shaped indentation 41 is designed, which forms a common clearance with the clearance situated between the stiffening elements 13 and the first decoupling region 32.

To the side bar 36 moreover a sealing lip 48 is assigned, which protrudes outwardly from the remaining second decoupling region 33 or the side bar 36 at an angle in the radial direction and extends up to the inner circumference 49 of the stiffening element 13. The sealing lip 48 is preferably designed to be circumferential. It is in contact with the inner circumference 48 in a sealing fashion and thus interacts with the inner circumference 49 in a sealing way. The sealing lip 48 has the advantage that, on the one hand, the sound propagation towards the back can be fully subdued and, on the other hand, also a reliable sealing of the membrane 21 against dirt and liquid is ensured.

The decoupling ring 6 consequently is pressed in both axially between the sensor housing and the protrusion 39 as well as radially between the membrane 21 and the inner circumference 49 and jammed in there.

Figure 2:
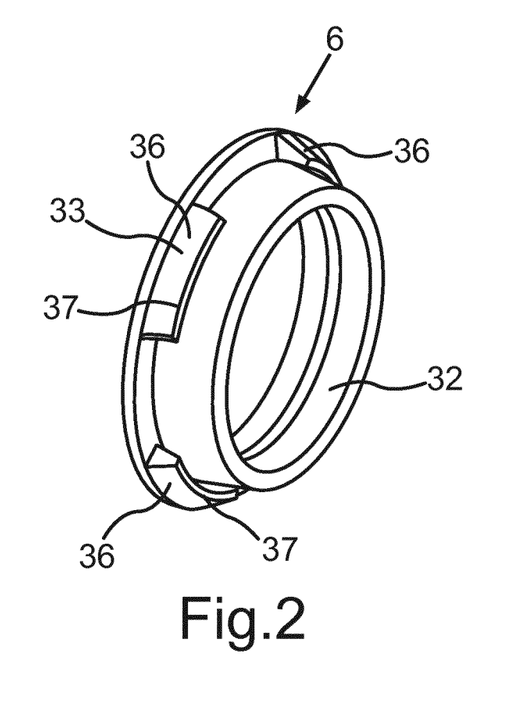
FIG. 2 a schematic view of the first embodiment of a decoupling ring.
Figure 3:
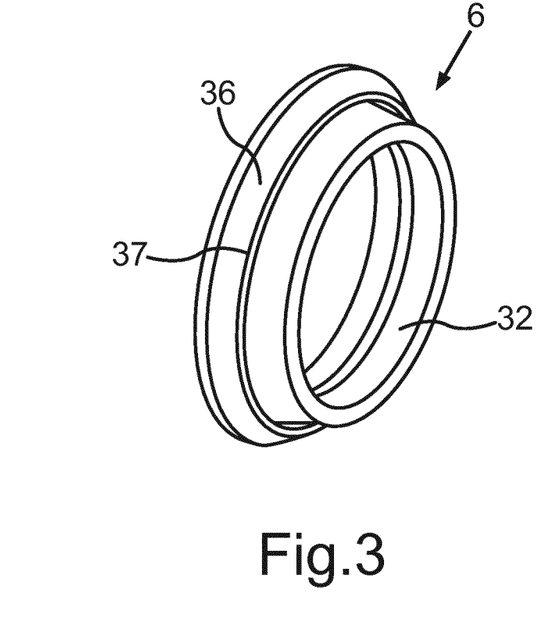
FIG. 3 a schematic view of a second embodiment of the decoupling ring.
Figure 4:
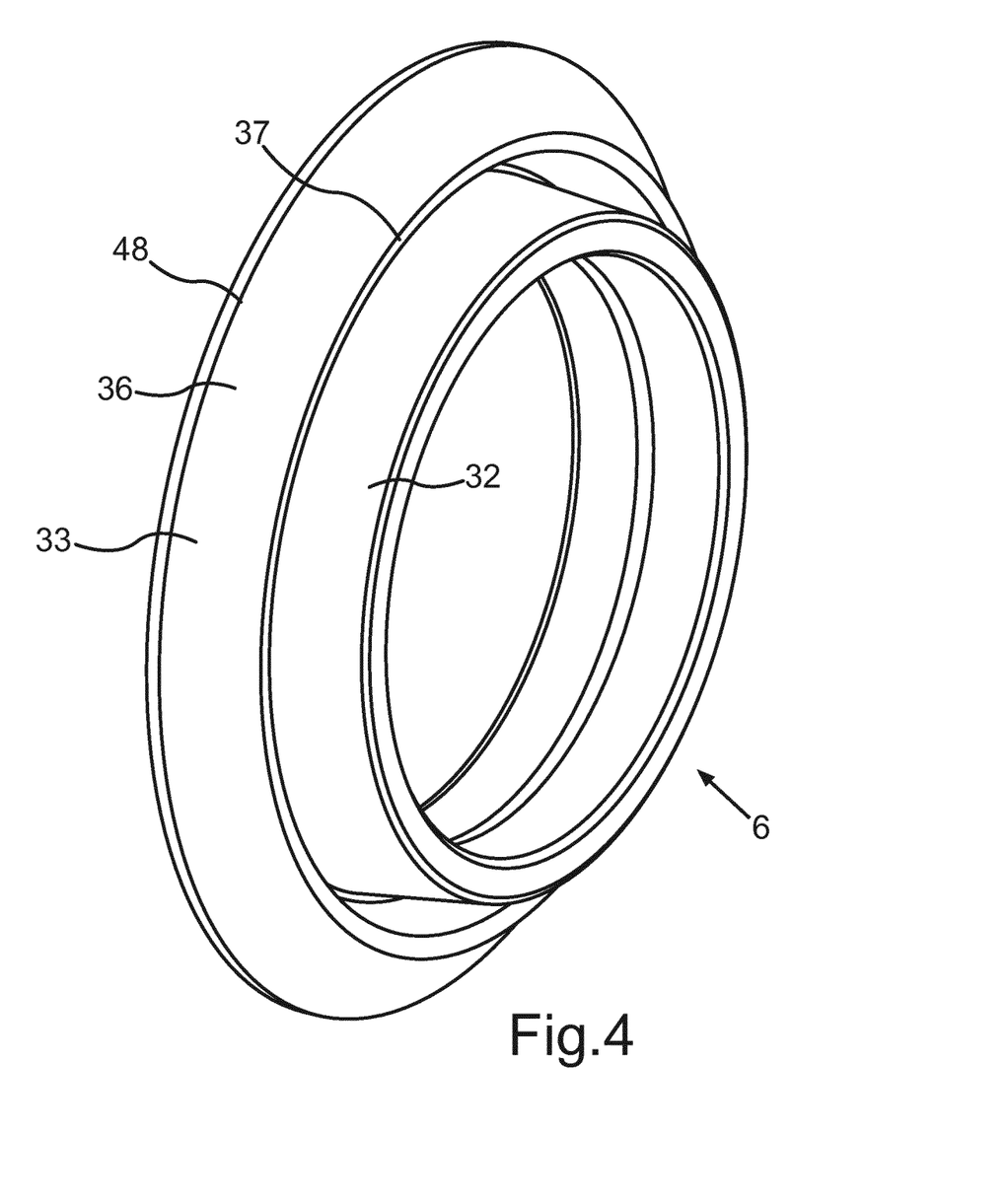
FIG. 4 a schematic view of a third preferred embodiment of a decoupling ring.

The side bar 36 in this connection can be a single side bar, which is arranged circumferentially or completely and uninterruptedly around the membrane 21 so that a circumferential and ring-shaped contact between the second decoupling region 33 and the protrusion 39 is given. Alternatively, however, it can also be envisaged that several side bars 36 are arranged to be distributed spaced apart from each other in the circumferential direction of the membrane 21. Correspondingly, also a single circumferential lip 48 can be envisaged or several such lips 48 can be provided, namely in particular as many as there are side bars 36. With reference to FIGS. 2 to 4 these embodiments are now explained in more detail:

In FIG. 2 in a perspective view in this connection a decoupling ring 6 is shown, in which several such side bars 36 with axial face 37 each are provided. As can be clearly seen from FIG. 2, these side bars 36 are arranged to be spaced apart from each other in the circumferential direction. For instance four or five such side bars 36 can be provided, which are arranged to be distributed equidistantly in the circumferential direction. In the example according to FIG. 2 the sealing lip 48 is not envisaged, but may nevertheless be provided with each side bar 36.

In FIG. 3, by contrast, a decoupling ring 6 is shown, in which a single side bar 36 with a circumferential front side 37 is provided. This means that this side bar 36 extends fully circumferentially on the outer circumference around the first decoupling region 32. Here, too, the sealing lip 48 is not shown, but may also be provided.

By contrast, the decoupling ring 6 according to FIG. 4 is designed to comprise such a lip 48. So this decoupling ring 6 on the whole corresponds to the ring according to FIG. 3, however with the difference that it comprises the sealing lip 48, which extends radially and axially outwardly at an angle.

All three decoupling rings 6 allow for a particularly reliable oppression of an echo and thus an oppression of the sound propagation behind the ultrasonic sensor 2 so that also reflections at the body elements of the motor vehicle can be avoided, as well as pseudo echoes. However, the ring 6 according to FIG. 4 is preferred.

Figure 5:
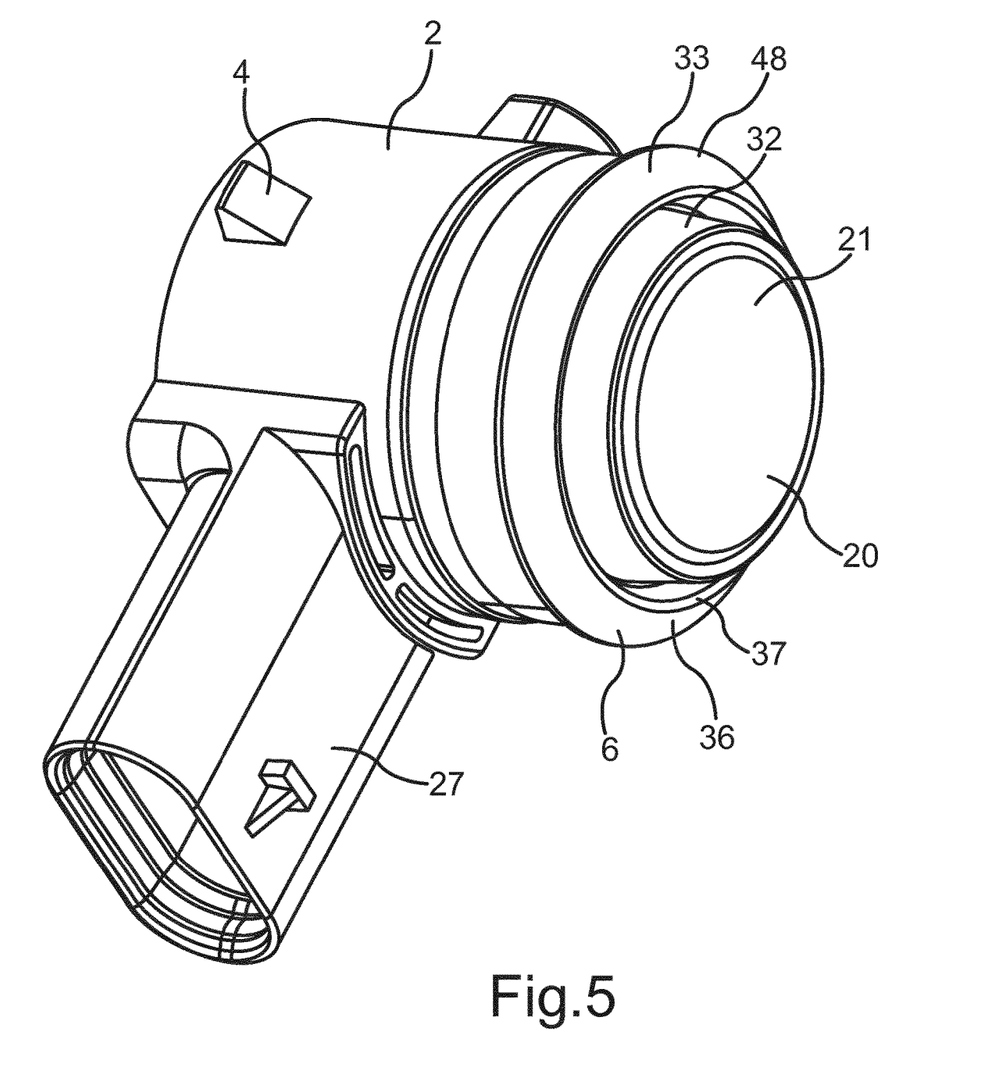
FIG. 5 a schematic and perspective view of an ultrasonic sensor with the decoupling ring according to FIG. 4.

An ultrasonic sensor 2 comprising such decoupling ring 6, as it is shown in FIG. 4, is shown in more detail in a perspective view in FIG. 5. The decoupling ring 6 is put on the pot-shaped membrane 21 from the axial front side or the front side 20. It thus contacts the outer circumference of the membrane 21 in a circumferential and sealing way. Moreover, here the outwardly protruding sealing lip 48 can be discerned particularly well.

Depending on the thickness of the trim element 30, its geometry, its material, as well as depending on the vehicle design behind the trim element it may be required to take further measures for oppressing the echo. This means that optionally the attenuation disk 7 is inserted between the stiffening element 13 and the receiving element 3. Making reference again to FIG. 6, the ring-shaped attenuation disk 7, which is adapted to the form of the stiffening element 13, has a back side, which faces plug 27 and is of an even and smooth design and is attached to contact the bottom 24 of the receptacle 23. A front 42 of the attenuation disk 7, which faces the stiffening ring 13, by contrast, has a sound reduction structure 43 for reducing the echo, which in the embodiment is a knob structure with a plurality of knobs 44 that are arranged to be evenly distributed and are situated in a plane perpendicular to the longitudinal axis 35. These knobs 44 face in the direction of the stiffening element 13 and with their tips are in contact with the back side 31 of the stiffening element 13.

Figure 8:
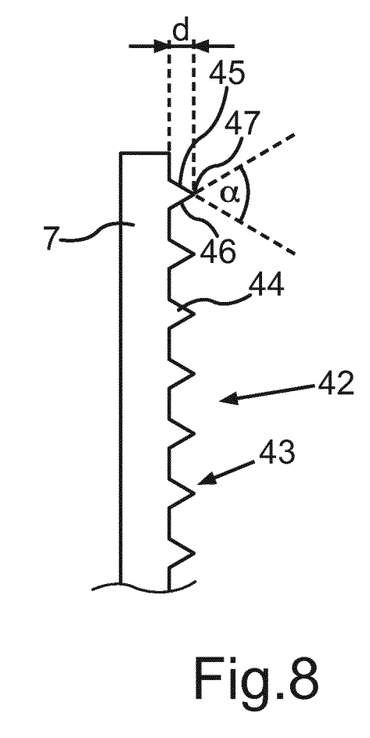
FIG. 8 a schematic sectional view of a section of an attenuation disk.

Now making reference to FIG. 8, in which a segment of the attenuation disk 7 is shown in a cross-sectional representation, the knobs 44 in the cross-section have the shape of a triangle with two legs 45, 46, which converge in a tapering way, whilst forming an angle α, and are brought together at a tip 47. In the embodiment the angle α is 60°. On the whole the knobs 44 have a conical shape with an opening angle α, wherein the tip 47 of this cone points in the direction of the stiffening element 13 and is in contact with its back side 31. A height d of this cone, i.e. the extension along a longitudinal axis 35, amounts for instance to 0.5 mm.

By such design of the attenuation disk 7 merely a dot-shaped or spotty contact with the stiffening element 13 is given so that thereby as well as due to the design of the knobs 44 a reliable sound oppression towards the back can be achieved.

The attenuation disk 7 in this connection can be designed as a separate component—possibly formed integrally with the decoupling ring 6. However, it may also be envisaged that this attenuation disk 7 is injection-moulded on the bottom 24 of the receptacle 23 so that the receptacle 3 and the attenuation disk 7 are integrally formed with each other.

The invention claimed is:

1. An ultrasonic sensor device for mounting adjacent a trim element of a motor vehicle, the ultrasonic sensor device comprising an ultrasonic sensor, which comprises a pot-shaped membrane for emitting and/or receiving ultrasonic signals, comprising a decoupling ring, which is arranged to fit around the membrane in contact with an outer circumference of the membrane, and comprising a stiffening element, which is arranged around the decoupling ring, wherein the decoupling ring comprises a circumferential first radial decoupling region which is in contact with the outer circumference of the membrane as well as a second radial decoupling region with an axial face, which is in contact with an axial face of the stiffening element, and wherein the axial face of the decoupling ring forms a front side, which faces in a first direction and is in contact with a back side of the stiffening element that faces the ultrasonic sensor and faces in a second direction, opposite the first direction.

2. The ultrasonic sensor device according to claim 1, wherein the second decoupling region is formed by at least one side bar which is arranged radially spaced apart from the first decoupling region and extends in the axial direction and the axial face of which is in contact with the axial face of the stiffening element.

3. The ultrasonic sensor device according to claim 2, wherein the at least one side bar is designed to taper off towards the axial face.

4. The ultrasonic sensor device according to claim 2, wherein the second radial decoupling region is formed by a single side bar which is designed to fit circumferentially around the first decoupling region.

5. The ultrasonic sensor device according to claim 2, wherein at least two side bars are arranged to be distributed spaced apart from each other in the circumferential direction, each of which comprises an axial face brought into contact with the axial face of the stiffening element.

6. The ultrasonic sensor device according to claim 1, wherein the first radial decoupling region is arranged at a radial distance from the stiffening element so that the decoupling ring touches the stiffening element exclusively via the second decoupling region.

7. The ultrasonic sensor device according to claim 1, wherein the second radial decoupling region comprises a radially outwardly extending sealing lip, which is in contact with a radial inner circumference of the stiffening element.

8. The ultrasonic sensor device according to claim 1, wherein the decoupling ring is formed from a soft elastic material, in particular from silicone and/or from TPE plastic.

9. The ultrasonic sensor device according to claim 1, wherein the ultrasonic sensor device comprises a holder for the ultrasonic sensor and the holder comprises a receiving element with a receptacle for the stiffening element, wherein between a bottom of the receptacle and a back side of the stiffening element which faces the ultrasonic sensor an attenuation disk is arranged for echo attenuation.

10. The ultrasonic sensor device according to claim 9, wherein the attenuation disk is formed from a soft elastic material, in particular from silicone and/or from TPE plastic.

11. The ultrasonic sensor device according to claim 9, wherein the attenuation disk at its front which faces the stiffening element comprises a sound reduction structure, in particular a knob structure for dot-shaped contact with the back side of the stiffening element.

12. The ultrasonic sensor device according to claim 9, wherein the attenuation disk is designed as a component which is separate from the receiving element.

13. The ultrasonic sensor device according to claim 9, wherein the attenuation disk is injection-moulded to the bottom of the receptacle of the receiving element.

14. The ultrasonic sensor device according to claim 9, wherein the attenuation disk is integrally formed with the decoupling ring.

15. The ultrasonic sensor device according to claim 9, wherein the attenuation disk is designed as a component which is separate from the decoupling ring.

16. The ultrasonic sensor device according to claim 1, in combination with a vehicle trim element, wherein the ultrasonic sensor device is mounted to the trim element with the front side of the stiffening element adjacent to the back side of the trim element and the trim element covers the sensor device such that the sensor device cannot be seen from the front side of the trim element.

17. In a motor vehicle, the ultrasonic sensor device according to claim 1 concealed on a back side of a trim element of the vehicle and oriented such that ultrasonic signals of the ultrasonic sensor are emitted or received through the material of the trim element.

* * * * *